United States Patent [19]

Kaiser et al.

[11] 4,011,319

[45] Mar. 8, 1977

[54] PHARMACEUTICAL COMPOSITIONS AND METHODS INVOLVING BENZAZEPINE DERIVATIVES

[75] Inventors: Carl Kaiser, Haddon Heights, N.J.; Robert G. Pendleton, Philadelphia, Pa.

[73] Assignee: SmithKline Corporation, Philadelphia, Pa.

[22] Filed: July 2, 1975

[21] Appl. No.: 592,708

[52] U.S. Cl. ............................................. 424/244
[51] Int. Cl.² ...................................... A61K 31/33
[58] Field of Search ................................... 424/244

[56] References Cited

UNITED STATES PATENTS 3,393,192   7/1968   Lewis et al. ................... 260/239

OTHER PUBLICATIONS

Allen et al., Chem. Abst., vol. 81 (1974), p. 99497z.

Primary Examiner—Sam Rosen
Attorney, Agent, or Firm—Richard D. Foggio; William H. Edgerton

[57] ABSTRACT

Pharmaceutical compositions and a method of stimulating peripheral dopamine receptors by administering internally a nontoxic effective quantity of a benzazepine derivative to an animal. Renal vasodilator and diuretic methods are also disclosed.

13 Claims, No Drawings

PHARMACEUTICAL COMPOSITIONS AND METHODS INVOLVING BENZAZEPINE DERIVATIVES

This invention relates to novel pharmaceutical compositions containing as an active ingredient compounds which are stimulants of peripheral dopamine receptors and to a method of stimulating peripheral dopamine receptors by administering nontoxic effective quantities of said active ingredients to an animal. In particular, the active ingredients used herein increase renal blood flow. As defined more fully below the active ingredients produce renal vasodilator activity and, in addition, most produce diuretic activity. Stimulants of peripheral dopamine receptors are therefore useful, for example, in hypertension, shock, congestive cardiac failure and renal insufficiency. Due to the potential for dilating cerebral blood vessels, dopamine agonists may also be useful in the treatment of cerebral artery spasm as in migraine or after subarachnoid hemorrhage.

Evidence has been accumulating to suggest that there are specific peripheral dopamine receptors located in the renal, mesenteric, coronary and cerebral vasculatures that produce vasodilation. The hypothesis is that localized renal vasodilation induced by dopaminergic receptor stimulation effectively lowers arterial blood pressure in hypertension. The goal for vasodilators specific for the renal vasculature is, by lowering renal vasculature resistance, to increase renal blood flow and produce natriuresis/diuresis thereby lowering blood pressure.

The active ingredients used in the compositions and methods of this invention are benzazepine derivatives represented by the following general structural formula:

FORMULA I

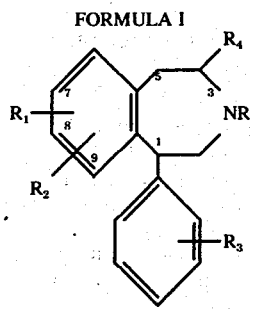

in which:
R is hydrogen, methyl, hydroxyethyl or n-butyl;
$R_1$ is hydrogen, hydroxy, methoxy, ethoxy or alkanoyloxy, in the 7-, 8- or 9-position;
$R_2$ is hydroxy, methoxy, ethoxy or alkanoyloxy, in the 8- or 9-position;
$R_3$ is hydrogen, chloro, bromo, fluoro, methyl, hydroxy or methoxy; and
$R_4$ is hydrogen or methyl,
or a pharmaceutically acceptable acid addition or quaternary salt thereof.

The alkanoyl moieties advantageously have from 2 to 5 carbon atoms, such as acetyl, pivaloyl and the like.

Preferably R and $R_4$ are hydrogen, $R_1$ and $R_2$ are hydroxy and $R_3$ is hydrogen or a meta- or para-substituent as defined above. A particularly advantageous compound of formula I is 7,8-dihydroxy-1-phenyl-2,3,4,5-tetrahydro-1H-3-benzazepine.

The pharmaceutically acceptable acid addition salts having the utility of the free bases of formula I, prepared by methods well known to the art, are formed with both inorganic or organic acids, for example: maleic, fumaric, benzoic, ascorbic, pamoic, succinic, bismethylensalicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. Similarly the quaternary salts include those prepared from organic halides such as methyl iodide, ethyl iodide, benzyl chloride and the like.

1-Phenyl-2,3,4,5-tetrahydro-1H-3-benzazepines have been described in U.S. Pat. No. 3,393,192; British patent specification No. 1,118,688; and Swiss Pat. No. 555,831, including general methods of preparation. However these references disclose very few specific compounds falling within the scope of formula I hereinabove. In addition there is no disclosure of the dopaminergic properties of such compounds and their utility in the methods of this invention.

It will be obvious to one skilled in the art that the compounds of formula I may be present as diastereoisomers which may be resolved into d, l optical isomers. Resolution of the optical isomers may be conveniently accomplished by fractional crystallization of their salts with optically active acids from appropriate solvents. Unless otherwise specified herein or in the claims, it is intended to include all isomers, whether separated or mixtures thereof. Where isomers are separated, the desired pharmacological activity will usually predominate in one of the isomers.

The compounds of formula I where R is hydrogen are generally prepared from intermediates of the following formula:

FORMULA II

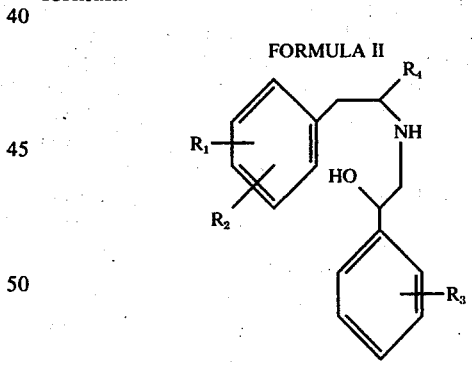

in which $R_1$ is hydrogen, methoxy or ethoxy; $R_2$ is methoxy or ethoxy; $R_3$ is hydrogen, chloro, bromo, fluoro, methyl or methoxy; and $R_4$ is hydrogen or methyl, by means of an intramolecular cyclization effected by reaction with a reagent such as sulfuric acid, polyphosphoric acid or a similar dehydrating agent. To obtain the benzazepine products wherein $R_1$, $R_2$ and $R_3$ are hydroxy, cyclization of the corresponding methoxy substituted intermediates is preferably carried out with 48% hydrobromic acid at reflux temperature for from 2 to 4 hours whereby simultaneous demethylation of the methoxy groups occurs.

Alternatively the compounds of formula I where R is hydrogen may be prepared from 1-phenyl-2-oxo- 2,3,4,5-tetrahydro-1H-3-benzazepine intermediates which are obtained by heating on appropriate phenylalkylamine with an ester of mandelic acid to give the amide. The latter is cyclized as described above to form the 2-oxo benzazepine intermediates which are chemically reduced, for example with borane in tetrahydrofuran, to the benzazepine products.

The compounds of formula I where $R_1$ and $R_2$ are both hydroxy, methoxy or ethoxy in the 8-and 9-positions are advantageously prepared from corresponding substituted intermediates such as those of formula II by chlorinating the latter and effecting cyclization with sulfuric acid to give the 6-chloro-8,9-dialkoxy substituted benzazepine. Catalytic hydrogenation in the presence of palladium-on-carbon removes the 6-chloro group. Treatment of the 8,9-dimethoxy benzazepine with for example boron tribromide affords the corresponding 8,9-dihydroxy product.

To prepare the compounds of formula I where R is hydroxyethyl or n-butyl, the corresponding benzazepines wherein R is hydrogen are alkylated with ethylene oxide or n-butyl bromide. Advantageously, to obtain the products where $R_1$ and/or $R_2$ are hydroxy the reaction with n-butyl bromide is carried out on the corresponding methoxy substituted benzazepines in an inert solvent such as methanol or acetone, preferably at reflux temperature and in the presence of a basic condensing agent such as potassium hydroxide or carbonate. Treatment of the resulting product with for example boron tribromide gives the hydroxy substituted benzazepines.

The compounds of formula I where R is methyl are conveniently prepared from methoxy substituted benzazepines where R is hydrogen by reaction with formic acid formaldehyde. Similar treatment of the resulting product with boron tribromide gives the corresponding hydroxy substituted benzazepines.

To prepare the compounds of formula I where $R_1$ or $R_2$ is alkanoyloxy, the corresponding 3-benzyl hydroxy substituted benzazepine (obtained by alkylation of the hydroxy benzazepine with benzyl bromide in the presence of potassium carbonate) is treated with the appropriate alkanoic acid anhydride, for example acetic anhydride and the resulting alkanoyloxy substituted benzazepine is hydrogenated in the presence of palladium-on-carbon to remove the protective benzyl group.

The intermediates of formula II above are generally prepared by heating equimolar amounts of a styrene oxide with a phenethylamine, each appropriately substituted, either alone or in an inert organic solvent such as tetrahydrofuran. Preferably the heating is effected on a steam bath or at reflux temperature for from 12 to 24 hours. The required styrene oxide is conveniently prepared by reaction of the ylide derivative from sodium hydride and trimethylsulfonium iodide with the appropriate benzaldehyde.

As stated above, the active ingredients used herein stimulate peripheral dopamine receptors, for example they increase renal blood flow. This renal vasodilator activity of the benzazepine compounds of formula I is measured in an anesthetized dog. In this pharmacological procedure, a test compound is administered either by rapid i.v. injection at doses of 1, 100 and 1000 mcg/kg or by infusion of 10 mcg/kg/min up to a maximum of 60 minutes to anesthetized normotensive dogs and the following parameters are measured: renal artery blood flow, femoral artery blood flow, arterial blood pressure and heart rate. Results are reported as a percent change, increase or decrease, at time of peak response (from controls) and for a significant effect renal blood flow (increase) and renal vascular resistance (decrease) should be approximately 10% or greater. The effect on renal vascular resistance can be calculated from any change in renal blood flow and arterial blood pressure. To confirm the mechanism of action, representative active renal vasodilator compounds are checked for blockade by bulbocapnine which is known to be a specific blocker of renal dopamine receptors. An advantageous compound of formula I, 7,8-dihydroxy-1-phenyl-2,3,4,5-tetrahydro-1H-3-benzazepine, in two dogs tested by i.v. injection as decribed above produced an average maximal change of +22% in renal blood flow and −47% in renal vascular resistance at an average dose to produce a maximal change in renal blood flow of 550 mcg/kg, with little direct effect on systemic blood pressure in normotensive animals.

In addition to the renal vasodilator activity, the benzazepine compounds of formula I except those where R is n-butyl or $R_1$ and $R_2$ are 8,9-dihydroxy or 8,9-dialkanoyloxy produce diuretic activity. Such diuretic activity is measured in the standard saline-loaded rat procedure. A test compound is administered i.p. at doses of from 10 to 40 mg/kg and the parameters measured are urine volume (hourly for three hours) plus sodium and potassium ion concentrations. 7,8-Dihydroxy-1-phenyl-2,3,4,5-tetrahydro-1H-3-benzazepine tested in the above procedure produced a significant increase in urine volume and natriuresis at a dose as low as 12.5 mg/kg, i.p. Similar results were obtained at oral doses of 50 or 100 mg/kg.

The compositions of this invention are prepared in conventional dosage unit forms by incorporating a compound of formula I or a pharmaceutically acceptable salt thereof, in a nontoxic amount sufficient to stimulate peripheral dopamine receptors in an animal, with a nontoxic pharmaceutical carrier according to accepted procedures. Preferably the compositions will contain the active ingredient in an active but nontoxic amount selected from about 20 mg. to about 1000 mg. of active ingredient per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul or for i.v. infusion, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to the desired end product.

The method of stimulating peripheral dopamine receptors in accordance with this invention comprises administering internally to an animal requiring stimulation of said peripheral dopamine receptors a compound of formula I or a pharmaceutically acceptable salt thereof, usually combined with a pharmaceutical carrier, in a nontoxic amount sufficient to stimulate said peripheral dopamine receptors. The active ingredient will be administered preferably in a dosage unit, in an active, nontoxic quantity selected from about 20 mg. to about 1000 mg. of the parent chemical of formula I. The route of administration may be orally or parenterally, the oral route being preferred. Advantageously equal doses will be administered three times a day with the daily dosage regimen being selected from about 60 mg. to about 3000 mg. For administration by i.v. infusion, for example over a 10 to 30 minute period, a total dose selected from about 0.5 mg. to about 50 mg. will be administered. When the method described above is carried out stimulation of peripheral dopamine receptors is produced with a minimum of side effects.

Similar administration as described for the above method will produce renal vasodilator activity and in addition, except for those compounds of formula I where R is n-butyl or $R_1$ and $R_2$ are 8,9-dihydroxy or 8,9-dialkanoyloxy, will produce diuretic activity.

The following examples illustrate specific pharmaceutical compositions and their use in accordance with the method of this invention and as such are not to be construed as limitations thereof.

EXAMPLE 1

| Ingredients | Mg. per Capsule |
|---|---|
| 7,8-Dihydroxy-1-phenyl-2,3,4,5-tetrahydro-1H-3-benzazepine (as an acid addition or quaternary salt) | 50 (free base) |
| Magnesium stearate | 2 |
| Lactose | 200 |

The above ingredients are thoroughly mixed and placed into hard gelatin capsules.

| Ingredients | Mg. per Tablet |
|---|---|
| 7,8-Dihydroxy-1-phenyl-2,3,4,5-tetrahydro-1H-3-benzazepine (as an acid addition or quaternary salt) | 250 (free base) |
| Corn starch | 30 |
| Polyvinyl pyrrolidone | 12 |
| Corn starch | 16 |
| Magnesium stearate | 3 |

The first two ingredients are thoroughly mixed and granulated. The granules obtained are dried, mixed with the remaining corn starch and magnesium stearate, and compressed into tablets.

The capsules or tablets prepared as in Examples 1 or 2 are administered orally to an animal requiring stimulation of peripheral dopamine receptors within the dose ranges set forth hereinabove. Similarly other compounds of formula I can be formulated in the same manner to give pharmaceutical compositions useful in the methods of this invention.

The following examples illustrate the chemical preparation of compounds of formula I and as such are not to be construed as limiting the scope thereof.

EXAMPLE 3

A mixture of 72 g. (0.4 mol) of 3,4-dimethoxyphenylethylamine and 48 g. (0.4 mol) of styrene oxide is heated on a steam bath under argon with stirring overnight. To the reaction mixture is added 200 ml. of 2:1/ethyl acetate: petroleum ether and seeded with N-[2-(3,4-dimethoxyphenylethyl]-2-phenyl-2-hydroxyethylamine. Stirring is continued for 15 minutes with chilling to crystallize N-[2-(3,4-dimethoxyphenyl)ethyl]-2-phenyl-2-hydroxyethylamine, m.p. 94.5°–96° C.

A mixture of 100 g. (0.332 mol) of the above prepared ethylamine and 700 ml. of 48% hydrobromic acid is refluxed for 2 hours. Cooling to room temperature crystallizes the product, 7,8-dihydroxy-1-phenyl-2,3,4,5-tetrahydro-1H-3-benzazepine hydrobromide, m.p. 282°–283° C. Neutralization of the salt in methanol with alkali followed by ether extraction furnishes the free base which can then be converted into other salts as described hereinabove.

EXAMPLE 4

A solution of 30.1 g. (0.1 mol) of N-[2-(3,4-dimethoxyphenyl)ethyl]-2-phenyl-2-hydroxyethylamine in 120 ml. of trifluoroacetic acid and 8.2 ml. of concentrated sulfuric acid is heated at reflux for 2 hours. After cooling to room temperature, the trifluoroacetic acid is removed under reduced pressure and 100 ml. of ice-water is added. This mixture is basified to pH 9–10 with 10% sodium hydroxide solution and thoroughly extracted with ethyl acetate. The extract is dried and evaporated to give 7,8-dimethoxy-1-phenyl-2,3,4,5-tetrahydro-1H-3-benzazepine as an oil. Various salts can readily be prepared from the free base. For example, 5 g. (0.0176 mol) dissolved in dry ether is treated with methanesulfonic acid dropwise until no further precipitate is formed. The solid is filtered and washed with dry ether to give 7,8-dimethoxy-1-phenyl-2,3,4,5-tetrahydro-1H-3-benzazepine methanesulfonate, m.p. 133°–136° C.

EXAMPLE 5

A mixture of 4.32 g. (0.0154 mol) of 7,8-dimethoxy-1-phenyl-2,3,4,5-tetrahydro-1H-3-benzazepine, 0.02 mol of n-butyl bromide and 0.02 mol of potassium hyroxide is dissolved in 120 ml. of dry methanol and refluxed for 48 hours. The reaction mixture is evaporated to dryness, taken up in ethyl acetate and filtered to remove inorganic salts. The filtrate is washed with water, dried and evaporated to give 3-n-butyl-7,8-dimethoxy-1-phenyl-2,3,4-tetrahydro-1H-3-benzazepine as an oil.

The 3-n-butyl benzazepine (0.0107 mol) is dissolved in 120 ml. of dry methylene chloride and 0.032 mol of boron tribromide is added dropwise at −10° C. The solution is warmed to room temperature and stirred for two hours. The excess boron tribromide is destroyed with methanol added dropwise with ice-cooling. The cold solution is refluxed on the steam bath to remove hydrogen bromide and then evaporated to yield 3-n-butyl-7,8-dihydroxy-1-phenyl-2,3,4,5-tetrahydro-1H-benzazepine hydrobromide, m.p. 231°–234° C.

EXAMPLE 6

A solution of 3.5 g. (0.0129 mol) of N-[2-(3-methoxyphenyl)ethyl]-2-phenyl-2-hydroxyethylamine in 40 ml. of 48% hydrobromic acid is refluxed for two hours and then concentrated to dryness. The solid residue (equal mixture of 7-hydroxy and 9-hydroxy benzazepines) is chromatographed on a silica gel column, eluting with methanol in chloroform to first remove the 7-hydroxy isomer and then to yield the product 9-hydroxy-1-phenyl-2,3,4,5-tetrahydro-1H-3-benzazepine hydrobromide, m.p. 134°–150° C. (int.).

EXAMPLE 7

A suspension of 4.84 g. of sodium hydride (57% mineral oil dispersion) in 70 ml. of dry dimethyl sulfoxide is heated at about 65° C. under argon with stirring for 1 hour. Dry tetrahydrofuran (75 ml.) is added and the resulting solution is cooled to −5° C. Trimethylsulfonium iodide (19 g., 92.8 mmol) is added very slowly and stirring is continued for about 5 minutes. A solution of 12.6 g. (92.8 mmol) of p-methoxybenzaldehyde in 120 ml. of tetrahydrofuran is added and the temperature is maintained at −5° C. After addition is completed the mixture is allowed to warm to room temperature, poured into water and extracted with ether. The extract is washed with saturated sodium chloride solution, dried and evaporated to give p-methoxystyrene oxide.

A mixture of 16 g. (88 mmol) of 3,4-dimethyoxyphenylethylamine and 13.5 g. (88 mmol) of p-methoxystyrene oxide is heated with stirring under argon on a steam bath overnight. A sample is withdrawn from the reaction mixture and chromatographed on a silica column, eluting with benzene ethyl acetate to isolate the pure product in crystalline form. To the remainder of the reaction mixture is added 100 ml. of ethyl acetate-hexane (1:1) and seeded with the crystalline product, with stirring and chilling. Filtration furnishes the product N-[2-(3,4-dimethoxyphenyl)ethyl]-2-hydroxy-2-(4-methoxyphenyl)ethylamine, m.p. 92° C.

A solution of 4.4 g. (13.3 mmol) of the above prepared ethylamine in 20 ml. of 48% hydrobromic acid is heated at reflux under argon for 2 hours. Cooling precipitates 7,8-dihydroxy-1-(4-hydroxphenyl)-2,3,4,5-tetrahydro-1H-3-benzazepine hydrobromide, m.p. 287°–289° C.

EXAMPLE 8

Following the procedure of Example 7 and employing 2.42 g. of sodium hydride, 9.46 g. of trimethylsulfonium iodide and 6.33 g. (0.046 mol) of m-methoxybenzaldehyde there is obtained m-methoxystyrene oxide.

A mixture of 16 g. (88 mmol) of 3,4-dimethoxyphenylethylamine and 14.1 g. (88 mmol) of m-methoxystyrene oxide is heated on a steam bath under argon with stirring for 24 hours. A 2:1 mixture of ethyl acetate-petroleum ether is added. Chilling and stirring crystallizes the product N-[2-(3,4-dimethoxyphenyl)ethyl]-2-hydroxy-2-(3-methoxyphenyl)ethylamine, m.p. 83°–84° C.

The above prepared ethylamine (6.4 g., 19.3 mmol) is dissolved in 45 ml. 48% hydrobromic acid and the solution is heated at reflux under argon for two hours. Evaporation yields 7,8-dihydroxy-1-(3-hydroxyphenyl)-2,3,4,5-tetrahydro-1H-3-benzazepine hydrobromide, m.p. 285° C. (decomp.).

EXAMPLE 9

Following the procedure of Example 7, 9.7 g. of sodium hydride, 38 g. of trimethylsulfonium iodide and 25.2 g. (0.185 mol) of o-methoxybenzaldehyde are reacted to give o-methoxystyrene oxide.

A mixture of 33,5 g. (0.185 mol) of 3,4-dimethoxyphenylethylamine and 28 g. of o-methoxystyrene oxide is heated with stirring under argon on a steam bath overnight. A sample is chromatographed to obtain a pure sample of the product. This pure seed and 200 ml. of 2:1 ethyl acetatepetroleum ether are added to the reaction mixture. Chilling and stirring yields the product N-[2-(3,4-dimethoxyphenyl)ethyl]-2-hydroxy-2-(2-methoxyphenyl)ethylamine. m.p. 88° C.

A solution of 5 g. (15 mmol) of the above prepared ethylamine in 35 ml. of 48% hydrobromic acid is heated at reflux under argon for 2 hours. The reaction mixture is evaporated and the hydrobromide salt is converted to the free base using bicarbonate and carbonate to pH 8.5 in water. The aqueous solution is extracted with ethyl acetate, the extract is dried and evaporated to give the free base. The latter is dissolved in methanol and treated with ethereal hydrogen chloride to give 7,8-dihydroxy-1-(2-hydroxyphenyl)-2,3,4,5-tetrahydro-1H-3-benzazepine hydrochloride, m.p. 278°–280° C.

EXAMPLE 10

A 5.10 g. (0.020 mol) sample of 7,8-dihydroxy-1-phenyl-2,3,4,5-tetrahydro-1H-3-benzazepine free base (obtained by solution of the hydrobromide salt in warm methanol-water, neutralizing with excess sodium carbonate solution and filtering and drying the resultant precipitate) is slurried in 100 ml. of 1:1 methanol-acetone. The slurry is stirred under nitrogen and chilled to about 0° C. Sodium bicarbonate (1.68 g., 0.020 mol) is added as a solid and to the stirred mixture is added 5.69 g. (0.040 mol) of methyl iodide in 60 ml. of acetone, dropwise over a two to three hour period. After addition is completed the mixture is allowed to warm to ambient temperature and stirred for about 40 hours. The reaction mixture is filtered and the filtrate is concentrated to yield additional solid. The combined solids are slurried in water to remove inorganic salts, filtered and the solid dried to give 7,8-dihydroxy-3,3-dimethyl-1-phenyl-2,3,4,5-tetrahydro-1H-3-benzazepinium iodide, m.p. ca. 250° (dec.).

The iodide salt is dissolved in warm aqueous methanol and passed down a column of 100 g. (wet weight) of quaternary ion exchange resin (Biorad A61×8 50–100 mesh) previously converted to the methanesulfonate form by conversion of the chloride form to the hydroxide form and the latter to the methanesulfonate form. A 250 ml. volume of aqueous methanol is collected and concentrated to give 7,8-dihydroxy-3,3-dimethyl-1-phenyl-2,3,4,5-tetrahydro-1H-3-benzazepinium methanesulfonate, m.p. 243°–247° C. (dec.).

EXAMPLE 11

A 3.7 g. (0.0145 mol) sample of 7,8-dihydroxy-1-phenyl-2,3,4,5-tetrahydro-1H-3-benzazepine is slurried in 25 ml. of acetone and 0.7 g. (0.016 mol, 10% excess) of ethylene oxide is added. The mixture is placed in a pressure bottle and stirred at ambient temperature for about 40 hours. The reaction mixture is then heated to 60°–80° C. for 30 minutes, cooled and filtered. Concentration of the filtrate gives a solid which is taken up in ethyl acetate and reprecipitated with ether. The solid thus obtained is dissolved in ethanol and treated with ethereal hydrogen chloride to yield 7,8-dihydroxy-3-(2-hydroxyethyl)-1-phenyl-2,3,4,5-tetrahydro-1H-benzazepine hydrochloride, m.p. 136°–137° C.

EXAMPLE 12

A mixture of 100 g. (0.55 mol) of 3,4-dimethoxyphenylethylamine and 66.2 g. (0.55 mol) of styrene oxide in 200 ml. of tetrahydrofuran is refluxed overnight. The solvent is removed in vacuo, about 500 ml. of n-butyl chloride is added and the mixture cooled slightly. Filtration furnishes N-[2-(3,4-dimethoxyphenyl)ethyl]-2-phenyl-2-hydroxyethylamine, m.p. 92°–93° C.

The above prepared ethylamine, 71.5 g. (0.238 mol), is dissolved in 400 ml. of acetic acid and the solution is cooled. To this solution is added 16.9 g. (0.238 mol) of chlorine gas over a 30 to 45 minute period. The reaction mixture is poured into water, made basic with 40% sodium hydroxide solution and about 250 ml. of ether is added to the stirred solution. The resulting solid is filtered to give N-[2-(2-chloro-4,5-dimethoxyphenyl)ethyl]-2-phenyl-2-hydroxyethylamine, m.p. 110°–113° C.

To 100 ml. of concentrated sulfuric acid is added the above ethylamine (10 g., 30 mmol) with stirring. After about 20 minutes the reaction mixture is poured over ice and extracted with ethyl acetate. The aqueous solution is made basic with sodium hydroxide pellets and 40% sodium hydroxide solution. The oil which forms is extracted with ether, the extract is dried and concentrated to about one-half volume. Ethereal hydrogen chloride is added to furnish 6-chloro-8,9-dimethoxy-1-phenyl-2,3,4,5-tetrahydro-1H-3-benzazepine hydrochloride, m.p. 209°–210° C.

The free base (14 mmol) of the above prepared benzazepine (obtained from the hydrochloride salt by the addition of 14 mmol of aqueous sodium hydroxide solution) is dissolved in 150 ml. of ethanol and made basic with 0.1 N sodium hydroxide. The mixture is hydrogenated in the presence of 250 mg. of 10% palladium-on-carbon in a Parr shaker for 8 hours at 65° C. The reaction mixture is allowed to stand overnight, filtered and the ethanol removed in vacuo. The residual mixture is extracted with chloroform, the extract is washed with brine and dried. Concentration gives an oil which is dissolved in ether, filtered and ethereal hydrogen chloride is added to give 8,9-dimethoxy-1-phenyl-2,3,4,5-tetrahydro-1H-3-benzazepine hydrochloride, m.p. 212°–214° C.

A solution of 8.55 g. (30.2 mmol) of the above dimethoxy benzazepine free base in 60 ml. of dry methylene chloride is cooled to −10° C. To this cooled solution is added cautiously 39.2 g. (150 mmol) of boron tribromide and upon completion of the addition the mixture is stirred at room temperature for about 1¼ hours. The reaction mixture is evaporated in vacuo and to the residue is added, very cautiously, small amounts of methanol to effect solution. The methanol is then removed in vacuo and the residue is dissolved in a minimal amount of hot water. A solid which is 8,9-dihydroxy-1-phenyl-2,3,4,5-tetrahydro-1H-3-benzazepine hydrobromide, m.p. 142° C. (dec.) crystallizes from the hot water.

EXAMPLE 13

A mixture of 42.0 g. of 57% sodium hydride dispersed in oil and 700 ml. of dimethyl sulfoxide is stirred at 70°–75° C. for 1 to 1¼ hours. The solution is diluted with 700 ml. of dry tetrahydrofuran and cooled to 0° C., under nitrogen. A 200 g. (1.0 mol) sample of trimethylsulfonium iodide is added in portions, maintaining the temperature between 0°–5° C. The mixture is stirred for 15 minutes and then a solution of 70.4 g. (0.50 mol) of m-chlorobenzaldehyde in 300 ml. of dry tetrahydrofuran is added dropwise. The resulting mixture is stirred a room temperature for 4 hours, poured into water and extracted with ether. The extract is washed with brine, dried and evaporated in vacuo to leave m-chlorostyrene oxide.

A solution of 27.1 g. (0.1 mol) of N-benzyl-3,4-dimethoxyphenylethylamine and 23.3 g. (0.15 mol) of m-chlorostyrene oxide in 500 ml. of methanol is stirred and refluxed overnight. The methanol is removed in vacuo and the residual N-benzyl-N-[2-(3,4-dimethoxyphenyl)ethyl]-2-hydroxy-2-(3-chlorophenyl)ethylamine is reduced without further purification. This sample (0.01 mol) is dissolved in ether, acidified with ethereal hydrogen chloride and hydrochloride precipitates. The latter is dissolved in 90 ml. of methanol, the solution is added to a mixture of 0.5 g. of palladium-on-carbon in 10 ml. of ethyl acetate and the mixture is hydrogenated at room temperature for 90 minutes at 60 psi. The reaction mixture is filtered and the filtrate evaporated in vacuo to yield N-[2-(3,4-dimethoxyphenyl)ethyl]-2-hydroxy-2-(3-chlorophenyl)ethylamine hydrochloride, m.p. 155°–157.5° C.

A solution of 6.0 g. (0.0161 mol) of the above prepared amine hydrochloride in 250 ml. of 48% hydrobromic acid is stirred and refluxed for 3 hours. The reaction mixture is evaporated in vacuo to give 1-(3-chlorophenyl)-7,8-dihydroxy-2,3,4,5-tetrahydro-1H-3-benzazepine hydrobromide, m.p. 231°–235° C.

EXAMPLE 14

Following the procedure of Example 13 and employing 42.0 g. of 57% dispersion of sodium hydride in mineral oil, 200 g. (1.0 mol) of trimethylsulfonium iodide and 70.4 g. (0.50 mol) of o-chlorobenzaldehyde there is obtained o-chlorostyrene oxide.

Similarly 2.71 g. (0.01 mol) of N-benzyl-3,4-dimethoxyphenethylamine and 2.33 g. (0.015 mol) of o-chlorostyrene oxide are reacted in methanol to give N-benzyl-N-[2-(3,4-dimethoxyphenyl)ethyl]-2-hydroxy-2-(2-chlorophenyl)ethylamine. The latter is converted to its hydrochloride, dissoved in 90 ml. of methanol and hydrogenated over 1 g. of 10% palladium-on-carbon in 10 ml. of ethyl acetate at room temperature for 6 hours. The reaction mixture is filtered and evaporated in vacuo to leave N-[2-(3,4-dimethoxyphenyl)ethyl]-2-hydroxy-2-(2-chlorophenyl)ethylamine hydrochloride, m.p. 128°–132° C.

A solution of 3.84 g. (0.0103 mol) of the above hydrochloride in 250 ml. of 48% hydrobromic acid is stirred and refluxed for 2 hours. The reaction mixture is evaporated in vacuo to yield 1-(2-chlorophenyl)-7,8-dihydroxy-2,3,4,5-tetrahydro-1H-3-benzazepine hydrobromide, m.p. 234°–235° C.

EXAMPLE 15

Following the procedure of Example 13 and employing 42.0 g. of 57% sodium hydride/mineral oil, 200 g.

(1.0 mol) of trimethylsulfonium iodide and 70.4 g. (0.50 mol) of p-chlorobenzaldehyde there is obtained p-chlorostyrene oxide.

Similarly 5.42 g. (0.02 mol) of N-benzyl-3,4-dimethoxyphenethylamine and 4.64 g. (0.03 mol) of p-chlorostyrene oxide are reacted in methanol to give N-benzyl-N-[2-(3,4-dimethoxyphenyl)ethyl]-2-hydroxy-2-(4-chlorophenyl)ethylamine. The hydrochloride of this ethylamine is dissolved in methanol and hydrogenated with 0.5 g. of 10% palladium-on-carbon in 10 ml. of ethyl acetate at room temperature and 60 psi. for about 90 minutes. The filtered reaction mixture is evaporated in vacuo to yield N-[2-(3,4-dimethoxyphenyl)ethyl]-2-hydroxy-2-(4-chlorophenyl)ethylamine hydrochloride, m.p. 167°–171° C.

A mixture of 5.0 g. (0.0134 mol) of this hydrochloride in 250 ml. of 48% hydrobromic acid is heated to reaction and then stirred and refluxed for 90 minutes. The reaction mixture is evaporated in vacuo to give 1-(4-chlorophenyl)-7,8-dihydroxy-2,3,4,5-tetrahydro-1H-3-benzazepine hydrobromide, m.p. 156°–164° C.

EXAMPLE 16

Sodium hydride (57%, 4.84 g., 0.115 mol) previously washed with hexane is stirred with 70 ml. of dimethylsulfoxide at 65°–70° C. for 2 hours under dry argon. The mixture is diluted with 70 ml. of dry tetrahydrofuran, cooled to −5° C. and 23.5 g. (0.115 mol) of trimethylsulfonium iodide in 100 ml. of dry dimethyl sulfoxide is added over a period of several minutes. After stirring for 1 minute 11.9 g. (0.0926 mol) of m-tolualdehyde is added at a moderate rate maintaining the temperature at 0° to −5° C. The mixture is stirred at 0° C. for 5 minutes and at room temperature for 1 hour, diluted with 500 ml. of ice-water and extracted with ether. The extract is washed with saturated sodium chloride solution, dried and evaporated to an oil, m-methylstyrene oxide.

A mixture of 14.5 g. (0.0797 mol) of 3,4-dimethoxyphenethylamine and 10.7 g. (0.0797 mol) of m-methylstyrene oxide is stirred at 100° C. under argon for 16 hours and then diluted with benzene. Cooling in ice precipitates N-[2-(3,4-dimethoxyphenyl)ethyl]-2-hydroxy-2-(3-methylphenyl)ethylamine, m.p. 95.5°–97° C.

The above prepared ethylamine (9.6 g., 0.0304 mol) is refluxed in 65 ml. of 48% hydrobromic acid for two hours under argon. Cooling yields the product 7,8-dihydroxy-1-(3-methylphenyl)-2,3,4,5-tetrahydro-1H-3-benzazepine hydrobromide, m.p. 108°–110° C.

EXAMPLE 17

Following the procedure of Example 16 and employing 57% sodium hydride (4.84 g., 0.115 mol), 23.5 g. (0.115 mol) of trimethylsulfonium iodide and 11.5 g. (0.0926 mol) of o-tolualdehyde there is obtained o-methylstyrene oxide.

Similarly a mixture of 13.6 g. (0.0753 mol) of 3,4-dimethoxyphenethylamine and 10.1 g. (0.753 mol) of o-methylstyrene oxide is stirred at 100° C. under argon for 16 hours to yield N-[2-(3,4-dimethoxyphenyl)ethyl]-2-hydroxy-2-(2-methylphenyl)ethylamine, m.p. 91°–94° C.

The above prepared ethylamine (8.5 g., 0.0269 mol) is refluxed in 58 ml. of 48% hydrobromic acid for 2 hours under argon. Cooling precipitates the product, 7,8-dihydroxy-1-(2-methylphenyl)-2,3,4,5-tetrahydro-1H-3-benzazepine hydrobromide, m.p. 232°–233° C.

EXAMPLE 18

Following the procedure of Example 16 and employing 4.84 g. (0.115 mol) of 57% sodium hydride, 23.5 g. (0.115 mol) of trimethylsulfonium iodide and 11.9 g. (0.099 mol) of p-tolualdehyde there is obtained p-methylstyrene oxide.

Similarly a mixture of 10.6 g. (0.0789 mol) of p-methylstyrene oxide and 14.3 g. (0.0789 mol) of 3,4-dimethoxyphenethylamine is stirred under argon and heated at 100° C. for 18 hours to yield N-[2-(3,4-dimethoxyphenyl)ethyl]-2-hydroxy-2-(4-methylphenyl)ethylamine, m.p. 99°–100° C.

The above prepared ethylamine (6.3 g., 0.02 mol) in 44 ml. of 48% hydrobromic acid is heated to reflux under argon for 2½ hours. Cooling yields 7,8-dehydroxy-1-(4-methylphenyl)-2,3,4,5-tetrahydro-1H-3-benzazepine hydrobromide, m.p. 261°–262° C.

EXAMPLE 19

A mixture of 20 g. (0.102 mol) of 1-(3,4-dimethoxyphenyl)-2-aminopropane and 12.01 ml. (0.102 mol) of styrene oxide is heated and stirred at 100° C. under argon for 18 hours. The cooled reaction mixture is dissolved in a minimum amount of benzene and petroleum ether is then added to precipitate a solid which turned to a liquid upon standing. Fractional vacuum distillation yields N-[2-(3,4-dimethoxyphenyl)-1-methylethyl]-2-hydroxy-2-phenylethylamine, b.p. 205°–225° C./0.2 mm.

To 4 g. (0.0132 mol) of the above prepared ethylamine is added 30 ml. of 48% hydrobromic acid and the mixture is heated to reflux for 2½ hours under argon. Cooling precipitates 7,8-dihydroxy-4-methyl-1-phenyl-2,3,4,5-tetrahydro-1H-3-benzazepine hydrobromide, m.p. 182°–184° C. (diastereomeric mixture).

EXAMPLE 20

A mixture of 20.0 g. (0.133 mol) of 4-methoxyphenylethylamine and 22.0 g. (0.133 mol) of methyl mandelate is heated at about 90° C. with stirring under nitrogen for 16 hours. The reaction mixture is taken up in ether and the product crystallized, giving N-[2-(4-methoxyphenyl)ethyl]mandelamide, m.p. 86°–88° C.

The above prepared amide (30 g., 0.105 mol) is added in several portions to about 1 l. of polyphosphoric acid, freshly prepared from 660 g. of phosphorus pentoxide and 330 ml. of 85% phosphoric acid. The additions are made with stirring and with the polyphosphoric acid initially at a temperature of 90° C. Following addition the reaction mixture is stirred for 1 hour, poured into ice-water with stirring and the resulting solid filtered and dried to give 8-methoxy-2-oxo-1-phenyl-2,3,4,5-tetrahydro-1H-3-benzazepine, m.p. 155°–170° C.

The benzazepine (8.9 g., 0.033 mol) is added in small portions to 75 ml. of cold (0° C.) 1 M borane in tetrahydrofuran. The mixture is stirred under nitrogen, allowed to warm to ambient temperature and the resulting solution is refluxed for 18 hours. The reaction mixture is allowed to cool, about 50 ml. of methanol is added cautiously and the solution refluxed for 1 hour. A 20 ml. portion of dilute hydrochloric acid is added and the mixture is refluxed an additional hour. The solution is cooled, filtered and concentrated to give the solid reduced benzazepine, m.p. 150°–160° C.

This material (8.25 g.) is added with stirring to 100 ml. of 48% hydrobromic acid, the mixture is stirred under nitrogen and heated to reflux. Reflux is continued for three hours and the reaction mixture is allowed to cool, depositing a white crystalline solid. Filtration yields 8-hydroxy-1-phenyl-2,3,4,5-tetrahydro-1H-3-benzazepine hydrobromide, m.p. 229°–233° C.

EXAMPLE 21

A solution of 3.58 g. (0.0126 mol) of 7,8-dimethoxy-1-phenyl-2,3,4,5-tetrahydro-1H-3-benzazepine in 15 ml. of formic acid and 10 ml. of formaldehyde is refluxed for 18 hours. The reaction mixture is evaporated to dryness, 20 ml. of 6N hydrochloric acid is added and the solution is again evaporated to dryness to give a liquid. The latter is treated with 20 ml. of 10% sodium hydroxide solution and the mixture is extracted with ether. The dried extract is evaporated to give the liquid 7,8-dimethoxy-3-methyl-1-phenyl-2,3,4,5-tetrahydro-1H-3-benzazepine.

The above prepared 3-methyl benzazepine (2.6 g., 0.00875 mol) is dissolved in 120 ml. of dry methylene chloride and 6.8 g. (0.027 mol) of boron tribromide is added dropwise at −10° C. The resulting solution is warmed to room temperature and stirred for 2 hours. The excess boron tribromide is destroyed with methanol, added dropwise with ice-cooling. The solution is refluxed on the steam bath to remove hydrogen bromide and then evaporated to dryness to furnish 7,8-dihydroxy-3-methyl-1-phenyl-2,3,4,5-tetrahydro-1H-3-benzazepine hydrobromide, 247°–249° C.

EXAMPLE 22

A 3.78 g. (0.009 mol) sample of 3-benzyl-7,8-dihydroxy-1-phenyl-2,3,4,5-tetrahydro-1H-3-benzazepine (prepared from the 3-unsubstituted benzazepine by reaction with benzyl bromide in the presence of potassium carbonate) is dissolved in 50 ml. of acetic anhydride and the solution is heated on a steam bath for 1 hour. The reaction mixture is cooled, ice-water is added and the solution is evaporated to dryness. The residue is triturated with ethyl acetate, the solution washed with ether, dried and the solvent removed in vacuo to leave an oil. The latter is dissolved in ether and etheral hydrogen chloride is added to precipitate 3-benzyl-7,8-diacetoxy-1-phenyl-2,3,4,5-tetrahydro-1H-3-benzazepine hydrochloride, m.p. 145°–150° C.

The diacetoxy compound prepared above, 3.5 g. (0.007 mol), is dissolved in 100 ml. of ethanol and 1 g. of 10% palladium-on-carbon is added. The mixture is hydrogenated in a Parr apparatus at 50° C. under 50 psi of hydrogen for 1 hour. The reaction mixture is filtered and the filtrate is evaporated to give 7,8-diacetoxy-1-phenyl-2,3,4,5-tetrahydro-1H-3-benzazepine hydrochloride, m.p. 170°–180° C.

EXAMPLE 23

A solution of 4.2 g. (0.01 mol) of 3-benzyl-7,8-dihydroxy-1-phenyl-2,3,4,5-tetrahydro-1H-3-benzazepine in 20 ml. of pivalic anhydride is heated on a steam bath for four hours. The reaction mixture is cooled and excess ethereal hydrogen chloride is added followed by 200 ml. of ether to precipitate 3-benzyl-7,8-bis(-pivaloyloxy)-1-phenyl-2,3,4,5-tetrahydro-1H-3-benzazepine hydrochloride, m.p. 248°–250° C.

This compound (2.68 g.) is dissolved in 100 ml. of ethanol and 1.0 g. of 10% palladium-on-carbon is added. The mixture is hydrogenated in a Parr apparatus at 37° C. under 50 psi of hydrogen for 4 hours. The reaction mixture is filtered and the filtrate is evaporated to dryness to yield 7,8-bis(pivaloyloxy)-1-phenyl-2,3,4,5-tetrahydro-1H-3-benzazepine hydrochloride, m.p. 275°–276° C.

What is claimed is:

1. A method of stimulating peripheral dopamine receptors in an animal requiring stimulation of said peripheral dopamine receptors which comprises administering internally to said animal a nontoxic amount sufficient to stimulate said peripheral dopamine receptors of a compound of the formula:

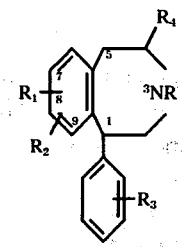

in which:
R is hydrogen, methyl, hydroxyethyl or n-butyl;
$R_1$ is hydrogen, hydroxy, methoxy, ethoxy or alkanoyloxy, in the 7-, 8-or 9-position;
$R_2$ is hydroxy, methoxy, ethoxy or alkanoyloxy, in the 8-or 9-position;
$R_3$ is hydrogen, chloro, bromo, fluoro, methyl, hydroxy or methoxy;
$R_4$ is hydrogen or methyl; and
said alkanoyl moieties have from 2 to 5 carbon atoms, or a pharmaceutically acceptable acid addition or quaternary salt of said compound.

2. The method of claim 1 in which R and $R_4$ are hydrogen, $R_1$ and $R_2$ are hydroxy, and $R_3$ is hydrogen or a meta-or para-substituent as defined above.

3. The method of claim 2 in which $R_1$ and $R_2$ are 7,8-dihydroxy and $R_3$ is hydrogen.

4. The method of claim 3 in which the compound is in the form of a free base.

5. The method of claim 3 in which the compound is in the form of a hydrobromide salt.

6. The method of claim 1 in which the active ingredient is administered with a pharmaceutical carrier in dosage unit form.

7. The method of claim 6 in which the administration is orally.

8. The method of claim 1 in which the active ingredient is administered with a pharmaceutical carrier by intravenous infusion.

9. The method of claim 1 in which a daily dosage selected from the range of about 60 mg. to about 3000 mg. of active ingredient is administered.

10. The method of claim 6 in which dosage units containing an active but nontoxic amount selected from about 20 mg. to about 1000 mg. of active ingredient are administered three times a day.

11. The method of claim 8 in which a total dose selected from the range of about 0.5 mg. to about 50 mg. of active ingredient is administered over a period of from 10 to 30 minutes.

12. A method of producing renal vasodilator activity in an aminal requiring said activity which comprises administering internally to said animal a nontoxic amount sufficient to produce said activity of a compound of the formula:

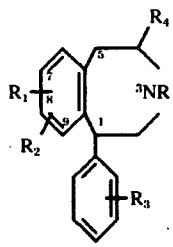

in which:
R is hydrogen, methyl, hydroxyethyl or n-butyl;
R₁ is hydrogen, hydroxy, methoxy, ethoxy or alkanoyloxy, in the 7-, 8-or 9-position;
R₃ is hydrogen, chloro, bromo, fluoro, methyl, hydroxy or methoxy;
R₄ is hydrogen or methyl; and
said alkanoyl moieties have from 2 to 5 carbon atoms, or a pharmaceutically acceptable acid addition or quaternary salt of said compound.

13. A method of producing diuretic activity in an aminal requiring said activity which comprises administering internally to said animal a nontoxic amount sufficient to produce said activity of a compound of the formula:

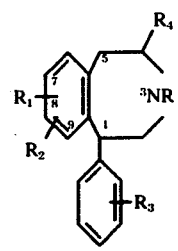

in which:
R is hydrogen, methyl or hydroxyethyl;
R₁ is hydrogen, hydroxy, methoxy, ethoxy or alkanoyloxy, in the 7-, 8-or 9-position;
R₂ is hydroxy, methoxy, ethoxy or alkanoyloxy, in the 8-or 9-position, provided that R₁ and R₂ are not 8,9-dihydroxy or 8,9-dialkanoyloxy;
R₃ is hydrogen, chloro, bromo, fluoro, methyl, hydroxy or methoxy;
R₄ is hydrogen or methyl; and
said alkanoyl moieties have from 2 to 5 carbon atoms, or a pharmaceutically acceptable acid addition or quaternary salt of said compound.

* * * * *

UNITED STATES PATENT AND TRADEMARK OFFICE
CERTIFICATE OF CORRECTION

PATENT NO. : 4,011,319
DATED : March 8, 1977
INVENTOR(S) : Carl Kaiser and Robert G. Pendleton It is certified that error appears in the above-identified patent and that said Letters Patent are hereby corrected as shown below:

Column 15, Claim 12, insert the following omission before line 19,

"$R_2$ is hydroxy, methoxy, ethoxy or alkanoyloxy, in the 8-or 9-position;"

Signed and Sealed this

Seventeenth Day of May 1977

[SEAL]

Attest:

RUTH C. MASON
Attesting Officer

C. MARSHALL DANN
Commissioner of Patents and Trademarks